(12) United States Patent
Yao et al.

(10) Patent No.: US 6,737,564 B2
(45) Date of Patent: May 18, 2004

(54) SELECTIVE MODIFICATION OF PLANT FATTY ACIDS

(75) Inventors: Kening Yao, Saskatoon (CA); David C. Taylor, Saskatoon (CA); Laurie Friesen, Saskatoon (CA); Roberto Bacchetto, Saskatoon (CA); Derek A. Potts, Saskatoon (CA)

(73) Assignee: Saskatchewan Wheat Pool, Regina (CA)

( * ) Notice: Subject to any disclaimer, the term of this patent is extended or adjusted under 35 U.S.C. 154(b) by 150 days.

(21) Appl. No.: 09/866,061

(22) Filed: May 25, 2001

(65) Prior Publication Data

US 2003/0056246 A1 Mar. 20, 2003

(51) Int. Cl.$^7$ ............................. A01H 1/00; A01H 5/00; A01H 5/10; C12P 7/64; C12N 15/82
(52) U.S. Cl. ...................... 800/306; 800/278; 800/281; 800/298
(58) Field of Search ................................ 800/278, 281, 800/298, 306; 536/23.1, 23.6

(56) References Cited

U.S. PATENT DOCUMENTS

| | | |
|---|---|---|
| 4,554,101 A | 11/1985 | Hopp |
| 4,684,611 A | 8/1987 | Schilperoort et al. |
| 4,743,548 A | 5/1988 | Crossway et al. |
| 4,801,540 A | 1/1989 | Hiatt et al. |
| 4,940,838 A | 7/1990 | Schilperoort et al. |
| 4,943,674 A | 7/1990 | Houck et al. |
| 4,945,050 A | 7/1990 | Sanford et al. |
| 5,015,580 A | 5/1991 | Christou et al. |
| 5,149,655 A | 9/1992 | McCabe et al. |
| 5,231,019 A | 7/1993 | Paszkowski et al. |
| 5,464,763 A | 11/1995 | Schilperoort et al. |
| 5,466,587 A | 11/1995 | Fitzpatrick-McElligott et al. |
| 5,501,967 A | 3/1996 | Offringa et al. |
| 5,510,255 A | 4/1996 | Knauf et al. |
| 5,584,807 A | 12/1996 | McCabe |
| 5,723,765 A | 3/1998 | Oliver et al. |
| 5,777,201 A | * 7/1998 | Poutre ........................ 800/205 |
| 5,866,789 A | * 2/1999 | Hildebrand .................. 800/205 |
| 6,495,738 B1 | * 12/2002 | Folkerts ...................... 800/281 |

OTHER PUBLICATIONS

Fourgoux–Nicol et al 1999, Plant Molecular Biology 40:857–872.*

Wang C. et al., J. of Agric. Food Chem.; 1996, vol. 44; pp. 3399–3402.*

Altschul et al., "Basic Local Alignment Search Tool," *J. Mol. Biol.* 215:403–410, 1990.

Ausubel et al., "Short Protocols in Molecular Biology," Fourth Edition, *Current Protocols in Molecular Biology*, pp. 2–34 through 2–44, 3–20 through 3–21, 1999.

Covello et al., "Recent Progress in the Molecular Farming of Squalene," *Advances in Plant Lipid Research*, 465–467, 1998.

Dellaporta et al., "A Plant DNA Minipreparation: Version II," *Plant Molecular Biology Reporter* 1(4):19–21, Fall 1983.

Dhein et al., "Effects of the gap junction uncoupler palmitoleic acid on the activation and repolarization wavefronts in isolated rabbit hearts," *British Journal of Pharmacology* 128:1375–1384, 1999.

Elledge et al., "λYES: A multifunctional cDNA expression vector for the isolation of genes by complementation of yeast and *Escherichia coli* mutations," *Proc. Natl. Acad. Sci. USA* 88:1731–1735, Mar. 1991.

Evans and Bravo, "Protoplast Isolation and Culture," *Handbook of Plant Cell Culture*, Macmillan Publishing Co., N.Y., 124–176, 1983.

Fraley et al., "Liposome–mediated delivery of tobacco mosaic virus RNA into tobacco protoplasts: A sensitive assay for monitoring liposome–protoplast interactions," *Proc. Natl. Acad. Sci. USA* 79:1859–1863, Mar. 1982.

Fraley et al., "Expression of bacterial genes in plant cells," *Proc. Natl. Acad. Sci. USA* 80:4803–4807, Aug. 1983.

Fromm et al., "Expression of genes transferred into monocot and dicot plant cells by electroporation," *Proc. Natl. Acad. Sci. USA* 82:5824–5828, Sep. 1985.

Gordon–Kamm et al., "Transformation of Maize Cells and Regeneration of Fertile Transgenic Plants," *The Plant Cell* 2:603–618, Jul. 1990.

Horsch et al., "Inheritance of Functional Foreign Genes in Plants," *Science* 223:496–498, 1983.

Klee et al., "Agrobacterium–Mediated Plant Transformation and its Further Applications to Plant Biology," *Ann. Rev. Plant Physiol.* 38:467–486, 1987.

Klein et al., "High–velocity microprojectiles for delivering nucleic acids into living cells," *Nature* 327:70–73, May 7, 1987.

Krens et al., "In vitro transformation of plant protoplasts with Ti–plasmid DNA," *Nature* 296:72–74, Mar. 4, 1982.

Needleman et al., "A General Method Applicable to the Search for Similarities in the Amino Acid Sequence of Two Proteins," *J. Mol. Biol.* 48:443–453, 1970.

Nestel et al., "Effects of increasing dietary palmitoleic acid compared with palmitic and oleic acids on plasma lipids of hypercholesterolemic men," *Journal of Lipid Research* 35:656–662, 1994.

Paszkowski et al., "Direct gene transfer to plants," *The EMBO Journal* 3(12):2717–2722, 1984.

(List continued on next page.)

Primary Examiner—David T. Fox
Assistant Examiner—Russell Kallis
(74) *Attorney, Agent, or Firm*—Klarquist Sparkman, LLP

(57) ABSTRACT

In various embodiments, the invention provides for the use of an ADS1 or ADS2 Δ9 fatty acid desaturase to selectively increase the relative proportion of oleic acid in the fatty acid of a plant part, such as in the oil of a mature seed. In some embodiments, the proportion of oleic acid may be increased preferentially, without a corresponding or proportional increase in palmitoleic acid.

30 Claims, 5 Drawing Sheets

OTHER PUBLICATIONS

Pearson and Lipman, "Improved tools for biological sequence comparison," *Proc. Natl. Acad. Sci. USA* 85:2444–2448, Apr. 1988.

Simon et al., "Serum Fatty Acids and Blood Pressure," *Hypertension* 27(2):303–307, Feb. 1996.

Smith and Waterman, "Comparison of Biosequences," *Advances in Applied Mathematics* 2:482–489, 1981.

Fukuchi–Mizutani et al., "Characterization of Δ9 Acyl–lipid Desaturase Homologues from *Arabidopsis thaliana*," *Plant Cell Physiol.* 39:247–253, 1998.

* cited by examiner

SELECTIVE MODIFICATION OF PLANT FATTY ACIDS

FIELD OF THE INVENTION

The present invention relates generally to modification of plant fatty acid composition by expression of a plant Δ9 acyl-CoA desaturase, particularly selective and preferential increases in the ratio of oleic acid to stearic acid.

BACKGROUND OF THE INVENTION

Lipids are essential in the composition of all plant cells. Although plant lipids cover a wide range of compounds, the majority of lipids are derived from two important metabolic pathways, the fatty acid biosynthetic pathway and the glycerolipid biosynthetic pathway. Plants naturally produce an assortment of fatty acids which they incorporate into a wide assortment of lipids which perform different functions. Polar glycerolipids (phospholipids and glycolipids), for example, contain two fatty acids attached to both sn-1 and sn-2 positions of the glycerol backbone and a polar headgroup attached to the sn-3 position. Polar glycerolipids play an essential role in cell membrane structure and function. Triacylglycerols, on the other hand, have all three positions of the glycerol backbone esterified with fatty acids and are the major storage lipids in oil-producing plant tissues, such as in plant seeds, and are usually known as plant oils.

The specific properties of a plant oil are dependent on the fatty acid composition of the oil, which in turn affects the nutritional quality of the oil. The health value of high levels of monounsaturates, particularly oleic acid, as the major dietary fat constituent has been established by recent studies. For example, canola oil, which typically contains at least 60% oleic acid (c18:1, Δ9), has been proven effective in lowering cholesterol in human blood. It has also been shown, however, that high levels of all monounsaturated fatty acids are not necessarily beneficial. For example, it has been suggested that palmitoleic acid (c16:1, Δ9) may have certain health disadvantages, such as behaving as a saturated fatty acid in its effect on cholesterol (Nestel et al., 1994, J Lipid Res 35(4):656–662) effecting atrioventicular conduction in the heart (Dhein et al, 1999, Br. J. Pharmacol 128(7) 1375–1384) and correlating with high blood pressure in men at high risk of coronary heart disease (Simon et al., Hypertension Feb. 27, 1996 (2):303–7). As a result, because of these medical and nutritional effects, there is an interest in lowering the level of saturated fatty acids in plant oils beyond certain limits (the limit of allowable saturated fatty acid proportions in canola oil, for example, is 7%).

The fatty acid composition of plant oils is determined both by the genotype of the plant and the plant's response to environmental factors such as light, temperature and moisture. Genetic modification by plant breeding or genetic engineering may be used to modify fatty acid metabolic pathways and thereby modify plant oil composition.

In plants, fatty acids are generally synthesized in the plastid or chloroplast by the FAS system in which the elongating chain is generally esterified to acyl-carrier protein (ACP) as palmitic acid (16:0) and stearic acid (18:0) esterified to ACP (i.e., 16:0-ACP and 18:0-ACP, respectively). A known soluble plant stearoyl-ACP Δ9 desaturase enzyme is located in the chloroplast where it is understood to catalyze the conversion of stearoyl-ACP (18:0-ACP) to oleoyl-ACP (18:1-ACP). These acyl-ACPs may either be used for glycerolipid synthesis in the chloroplast or transported out of chloroplast into the cytoplasm as acyl-CoAs. It is generally believed that the stearoyl-ACP Δ9 enzyme is the only soluble plant desaturase, so that palmitic acid and stearic acid exported from the chloroplast will not undergo further desaturation. Therefore, the level of saturation is largely determined by the amount of saturated fatty acids exported out of the chloroplast and into the cytoplasm.

This situation in plants is in contrast to that known for yeast and mammalian acyl-CoA Δ9 desaturases, which use fatty acids esterified to CoA as substrates, and desaturate both the saturated fatty acids palmitic acid and stearic acid. Mammalian and yeast acyl-CoA Δ9 desaturases have been used to modify levels of saturated fatty acids in plant tissues (U.S. Pat. Nos. 5,866,789 and 5,777,201) and have been shown to result in increased levels of monounsaturated fatty acids, including both oleic and palmitoleic fatty acids, and decreased levels of saturated fatty acids in plant oils. Recently, two genes homologous to the mammalian and yeast acyl-CoA desaturases were isolated from Arabidopsis, ADS1 and ADS2 respectively (Fukuchi-Mizutani et al. (1998) Plant Cell Physiol. 39:247–253). ADS1 and ADS2 share 76% amino acid sequence identity and it has been speculated that these two genes are Δ9 fatty acid desaturases. The Genbank database accession for the ADS1 protein and nucleic acid sequences is D88536, which sets out the sequences as follows:

(SEQ ID NO: 9)

```
MSLSASEKEENNKKMAADKAEMGRKKRAMWERKWKRLDIVKAFASLFVHF
LCLLAPFNFTWPALRVALIVYTVGGLGITVSYHRNLAHRSFKVPKWLEYF
FAYCGLLAIQGDPIDWVSTHRYHHQFTDSDRDPHSPNEGFWFSHLLWLFD
TGYLVEKCGRRTNVEDLKRQWYYKFLQRTVLYHILTFGFLLYYFGGLSFL
TWGMGIGVAMEHHVTCLINSLCHVWGSRTWKTNDTSRNVWWLSVFSFGES
WHNNHHAPESSARQGLEWWQIDISWYIVRFLEIIGLATDVKLPSESQRRR
MAMVR
```

(SEQ ID NO: 1)

```
ccacaaagag tcttttttt ttttctcttc gacttagctt
atacatagtt ttattacaag atgtcattgt cagcctcgga
gaaggaggag aataacaaga aaatggcagc ggacaaggct
gagatgggga ggaagaagag ggcaatgtgg gaaagaaagt
ggaagagatt ggacattgtg aaagcttttg catctctctt
tgtccatttc ctctgtctct tggcgccttt caatttcact
tggccggctt taagagtcgc cctcattgtc tatacggtgg
gtgggctcgg tatcaccgtc tcttaccacc gaaatttggc
tcaccggagc ttcaaagtcc ctaaatggct cgagtatttc
ttcgcttatt gcggccttct tgccattcag ggagatccga
ttgattgggt gagcacacat cgataccatc accagtttac
agattcggat agggacccac atagtcctaa cgaaggattt
tggttcagtc acctcctatg gctatttgat accggttatc
ttgtagaaaa gtgtggaaga aggacaaatg tggaggactt
aaagaggcag tggtactata aattcctcca aagaacagtc
```

-continued

```
ctttaccaca ttctaacatt tggtttcctc ctctattact
ttggtggttt gtcttttctt acttggggaa tgggtattgg
ggtagcaatg gagcatcatg tgacttgcct cataaactct
ctttgccatg tttggggaag ccgaacttgg aagactaatg
acacttcccg taacgtttgg tggctatcag tattctcgtt
tggagagagc tggcacaaca atcaccacgc cttcgaatcc
tcggcgagac aaggcttaga atggtggcaa atcgacattt
cttggtatat tgtccgcttt ctcgagatta tcggtttggc
tactgatgtt aagttgcctt ccgagagtca acgtcgtcgt
atggcaatgg ttcgttgaag atatggaacg acgtctcgtc
tcatttaagc attagttaat taatgtctac gtacgtttta
agtttttggt aaacgtaaca cttgtaatat tgtgcgatgc
ggtgttgttt tgtgacttgt ggtgtgtgtt tgaaccaact
tgcttaatta agataacgtt cgttttgata tgagcgaaaa
aaaaaaaaaa aaaaaaaa
```

The Genbank database accession for the ADS2 protein and nucleic acid sequences is D88537, which sets out the sequences as follows:
(SEQ ID NO: 10)

MSVTSTVEENHQKNPSTPAAVEEKKKRRWVFWDRRWRRLDYVKFASFTVH

SLALLAPFYFTWSALWVTFLFYTIGGLGITVSYHRNLAHRSFKVPKWLEY

LLAYCALLAIQGDPIDWVSTHRYHHQFTDSERDPHSPKEGFWFSHLLWIY

DSAYLVSKCGRRANVEDLKRQWFYRFLQKTVLFHILGLGFFLFYLGGMSF

VTWGMGVGAALEVHVTCLINSLCHIWGTRTWKTNDTSRNVWWLSVFSFGE

SWHNNHHAFESSARQGLEWWQIDISWYIVRFFEIIGLATDVKVPTEAQRR

RMAIVR (SEQ ID NO: 2)

```
gagaagagaa agagagatcc gaaatgtcgg tgacatcaac
ggtggaggag aaccaccaga aaaatccatc aacgccggcg
gcggtggagg agaagaagaa gaggagatgg gtgttttggg
atagaaggtg gaggagatta gattatgtga aattctcagc
ttctttcact gttcattctc ttgctctctt ggctccgttt
tatttcactt ggtcggctct ttgggttacg tttttgtttt
acaccatcgg tggtcttggt atcaccgtct cttatcatcg
caacttggct caccggagtt tcaaagtccc taaatggctt
gagtatctct tagcctattg tgcccttctc gctattcagg
gagatccgat tgattgggtg agtacacatc gttaccatca
ccagttcacg gattcagaac gtgatccaca tagtcctaag
gaaggttttt ggtttagtca tcttctttgg atctatgact
ctgcctatct tgtttcaaag tgtggaagaa gagcaaacgt
ggaggatttg aagaggcaat ggttttatag gtttcttcag
aaaacagtgc tatttcacat tttaggattg ggtttctttc
tcttctacct tggtggcatg tccttcgtta cttggggaat
gggggtagga gcagcattgg aagtgcacgt gacttgcctc
ataaattcac tctgccatat ttggggcact cgaacttgga
agaccaatga cacttctcgt aatgtttggt ggttatcggt
attttcattt ggagagagtt ggcacaacaa tcatcatgcg
ttcgagtcat cggctagaca aggacttgaa tggtggcaaa
tagacatttc gtggtacatt gttcggtttt tcgaaattat
cggtttagcg accgatgtga aagtgccaac ggaggctcaa
cgacgtcgta tggctatagt tcgttgatgg aaattgcggg
aagagcatag aaaaagggat ctattctatg taattagaat
aatttctaat cctaaaagag agttattgtt ttattttctt
tattactact tttgaagttt tgggttaacg caaaggacgt
ttccgatgtg ttttggtgtt ggaccaagtt gattaagata
tttgtcgtaa aaaaaaaaaa aaaaaaaaaa ctcgag
```

In view of the influence on health and nutrition, there is a continuing need for methods for modifying the fatty acid composition of plant parts, such as plant oils.

SUMMARY OF THE INVENTION

In various embodiments, the invention provides for the use of a ADS1 or ADS2 Δ9 fatty acid desaturase to selectively increase the relative proportion of oleic acid in the fatty acid of a plant part, such as in the oil of a mature seed. In some embodiments, the proportion of oleic acid may be increased preferentially, without a corresponding or proportional increase in palmitoleic acid.

In one aspect, the invention provides a method for modifying the fatty acid content of a plant part, such as an oil-producing plant tissue. In one aspect, the method may comprise the step of introducing a DNA sequence encoding an ADS1 or ADS2 Δ9 fatty acid desaturase into a plant cell of the plant, or an ancestor of the plant, to produce a genetically modified plant comprising the DNA sequence. The genetically modified plant may be maintained under conditions so that the DNA sequence encoding the ADS1 or ADS2 Δ9 fatty acid desaturase is expressed. The ratio of oleic acid (18:1) to stearic acid (18:0) may be increased by a selected value, such as by at least 20%, in a part of the genetically modified plant, compared to a corresponding part of a non-modified plant. The ratio of palmitoleic acid (16:1) to palmitic acid (16:0) in the part of the plant may also be decreased or remain unchanged or increase by an amount less than a selected value, such as by no more than 20%, compared to the corresponding part of the non-modified plant.

In one aspect, the invention provides genetically modified plants comprising a heterologous DNA sequence encoding an ADS1 or ADS2 Δ9 fatty acid desaturase. The DNA sequence encoding the ADS1 or ADS2 Δ9 fatty acid desaturase may be expressed so that the ratio of oleic acid (18:1) to stearic acid (18:0) is increased, for example it may be increased by at least 20%, in a part of the genetically modified plant, compared to a corresponding part of a non-modified plant. The ratio of palmitoleic acid (16:1) to palmitic acid (16:0) may also be decreased or remain unchanged or increased by no more than a selected value, such as 20%, in the part of the genetically modified plant.

In another aspect, the invention provides plant parts, such as an oil obtainable from an oil-producing plant tissue (such as from seeds), wherein the plant part has an increased ratio of oleic acid to stearic acid.

DETAILED DESCRIPTION OF THE INVENTION

Figure 1:
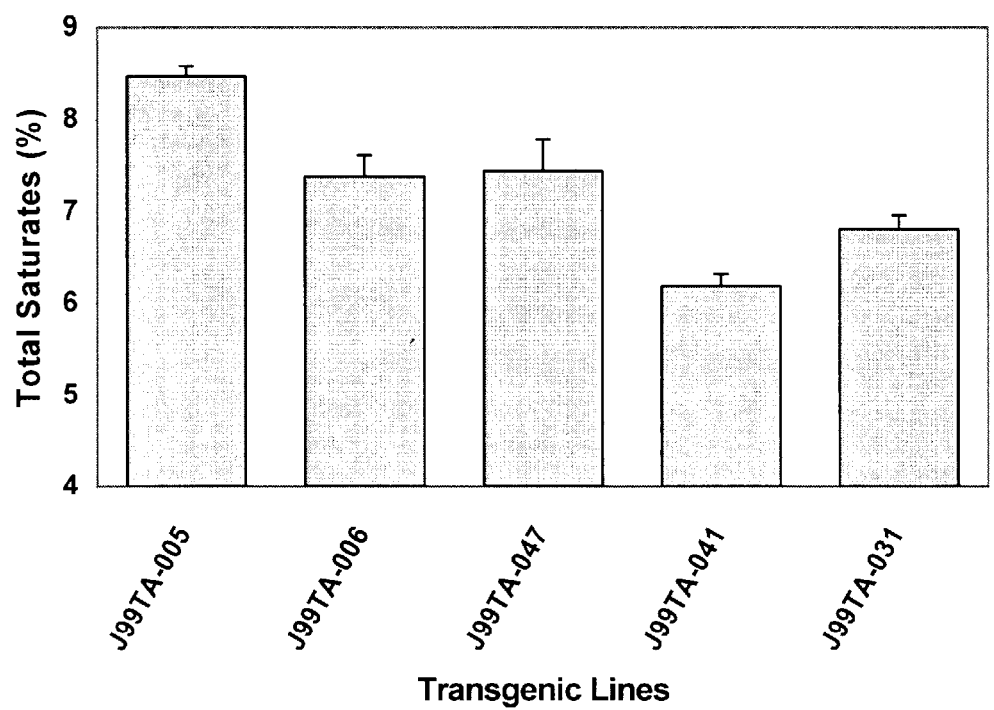
FIG. 1 is a bar graph showing the results of the experiments of Examples 5 and 6, showing changes of percentage of total saturated fatty acids in the representative T1 seeds of transgenic lines. ADS1 Positive lines are J99TA-31 and J99TA-41 (multiple copies ADS1). ADS1 Negative Lines are J99TA-05, J99TA-06 and J99TA-47.

In one aspect, the invention provides for the use of an ADS1 or ADS2 Δ9 fatty acid desaturase in plants. The ADS1 or ADS2 desaturase may for example be selective for a stearic acid substrate, to selectively increase the proportion of oleic acid in plant oils.

The term "fatty acid desaturase" refers to an enzyme which catalyzes the breakage of a carbon-hydrogen bond and the introduction of a carbon-carbon double bond into a fatty acid molecule. "Δ9 fatty acid desaturase" refers to a fatty acid desaturase that catalyzes the formation of a double bond between carbon positions 9 and 10 (corresponding to carbon positions numbered from the carbonyl carbon).

An "ADS1 Δ9 fatty acid desaturase" of the invention is an enzyme that has substantial sequence identity to wild type ADS1 desaturase (Genbank Accession No. D88536). Similarly, an "ADS2 Δ9 fatty acid desaturase" is an enzyme that has substantial sequence identity to wild type ADS2 desaturase (Genbank Accession No. D88537). Unless a contrary indication is given, any reference herein to "ADS1" or "ADS2" means, respectively, an ADS1 or ADS2 Δ9 fatty acid desaturase. Substantial sequence identity for this purpose may for example be any value from 70% to 100% sequence identity, when sequences are optimally aligned (with gaps of up to 20 amino acids permitted as instances of non-identity) wherein conservative amino acid substitutions may be permitted as instances of sequence identity. As used herein, the term "conserved amino acid substitutions" refers to the substitution of one amino acid for another at a given location in the peptide, where the substitution conserves the character of the amino acid residue. In making such changes, substitutions of like amino acid residues can be made on the basis of relative similarity of side-chain substituents, for example, their size, charge, hydrophobicity and hydrophilicity.

Optimal alignment of sequences for comparisons of identity may be conducted using a variety of algorithms, such as the local homology algorithm of Smith and Waterman,1981, Adv. Appl. Math 2: 482, the homology alignment algorithm of Needleman and Wunsch, 1970, J. Mol. Biol. 48:443, the search for similarity method of Pearson and Lipman, 1988, Proc. Natl. Acad. Sci. USA 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, J. Mol. Biol. 215:403–10 (using the published default settings). Software for performing BLAST analysis may be available through the National Center for Biotechnology Information (through the internet at http://www.ncbi.nlm.nih.gov/). For protein comparisons, BLASTP may be used with defaults as follows: G=11 (cost to open a gap); E=1 (cost to extend a gap); E=10 (expectation value, at this setting, 10 hits with scores equal to or better than the defined alignment score, S, are expected to occur by chance in a database of the same size as the one being searched; the E value can be increased or decreased to alter the stringency of the search.); and W=3 (word size).

In some embodiments, conserved amino acid substitutions may be made where an amino acid residue is substituted for another having a similar hydrophilicity value (e.g., within a value of plus or minus 2.0), where the following hydrophilicity values are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

In one aspect, the invention provides genetically modified plants having a heterologous ADS1 or ADS2 coding sequence, which may be introduced into the plant, or an ancestor of the plant, by transformation with a recombinant gene construct. Genetically modified plants having a heterologous ADS1 or ADS2 coding sequence may have a modified fatty acid composition in one or more tissues. In some embodiments, total saturated fatty acids may for example be reduced and monounsaturated fatty acids may be increased. In some embodiments, the ratio of oleic acid to stearic acid may be altered. In some embodiments, the selectivity of the ADS1 or ADS2 enzyme may result in a selective increase in the ratio of oleic acid to stearic acid compared to any alteration of the ratio of palmitoleic acid to palmitic acid. For the purposes of such comparisons, genetically modified plants of the invention may be compared to control plants that are genetically identical to the modified plants except for the absence of the heterologous ADS1 or ADS2 coding sequence. In some embodiments, the ratio of oleic acid to stearic acid may be increased proportionately more than any increase in the ratio of palmitoleic acid to palmitic acid. In such embodiments, the proportionality of the change in the relevant fatty acid ratio may be expressed as a percentage of the value in a non-modified control plant or tissue. In alternative embodiments, for example, the increase in the ratio of oleic acid to stearic acid may be equal to or greater than 5%, 10%, 15%, 20%, 25%, 30%, 35%, 40%, 45%, 50% 55%, 60%, 65%, 70%, 75%, 100%, 125%, 150% or 200%. In alternative embodiments, in connection with such increases in the oleic to stearic acid ratio, the ratio of palmitoleic acid to palmitic acid may for example decrease, stay essentially the same, or increase by a value that is less than the proportionate increase in the oleic acid to stearic acid ratio. For example, in some embodiments, the ratio of oleic acid to stearic acid may be increased by 20% or more while the ratio of palmitoleic acid to palmitic acid may decrease or increase by less than 20% (in alternative embodiments any of the foregoing values, or other values from 5% to 200% or more, may be substituted for the value of 20% in this example, where the increase in the ratio of oleic acid to stearic acid remains greater than any increase in the ratio of palmitoleic acid to palmitic acid).

In alternative embodiments, plants or plant tissues or plant parts of the invention may have a ratio of oleic acid to stearic acid that is in excess of a certain value, such as being greater than a value from 35 to 50, such as 35, 40 or 45. In alternative embodiments, the ratio of palmitoleic acid to palmitic acid in such plants, plant tissues or plant parts may be maintained below a certain value, such as below 1, below 0.1 or below 0.05. These ratios may be combined in a formula to characterize plants of the invention: (18:1/18:0)/(16:1/16:0), such an equation divides the ratio of oleic to stearic acid by the ratio of palmitoleic acid to palmitic acid. In alternative embodiments, this value may for example be greater than 600, 700, 800 or 900 in plants, plant parts or plant tissues of the invention. In some embodiments, the ratio of oleic acid to palmitoleic acid may be greater than a certain value, such as greater than 200 or greater than 250.

In various aspects of the invention, an ADS1 or ADS2 coding sequence may be used as part of a recombinant gene construct. The recombinant gene construct may comprise the open reading frame coding for ADS1 or ADS2 operably linked to at least one suitable regulatory DNA sequence that acts to control transgene expression to produce active enzyme.

The term "recombinant" means that something has been recombined, so that when made in reference to a nucleic acid sequence the term refers to a sequence that is comprised of nucleic acid sequences that are joined together by means of molecular biological techniques. The term "recombinant" when made in reference to a protein or a polypeptide refers to a protein sequence which is expressed using a recombinant nucleic acid sequence.

As used herein to describe nucleic acid or amino acid sequences the term "heterologous" refers to molecules or portions of molecules, such as DNA sequences, that are artificially introduced into a particular host cell. Heterologous DNA sequences may for example be introduced into a host cell by transformation. Such heterologous molecules may include sequences derived from the host cell. Heterologous DNA sequences may become integrated into the host cell genome, either as a result of the original transformation of the host cells, or as the result of subsequent recombination events. The term "heterologous" when made in reference to a nucleic acid sequence may therefore refer to a nucleotide sequence which is ligated to, or is manipulated to become ligated to, a nucleic acid sequence to which it is not ligated in nature, or to which it is ligated at a different location in nature. The term "heterologous" therefore indicates that the nucleic acid sequence has been manipulated using genetic engineering, i.e. by human intervention.

A cell, tissue, organ, or organism into which has been introduced a foreign nucleic acid, such as ADS1 or ADS2 coding sequence, is considered "transformed", "transfected", or "transgenic". A transgenic or transformed cell or organism also includes progeny of the cell or organism and progeny produced from a breeding program employing a transgenic plant as a parent in a cross and exhibiting an altered phenotype resulting from the presence of a recombinant nucleic acid construct. A transgenic plant is therefore a plant that has been transformed with a heterologous nucleic acid, or the progeny of such a plant that includes the transgene. Such plants may also be referred to as "genetically modified" to indicate that the genetic composition of the plant has been modified by human intervention.

In accordance with one aspect of the invention, methods are provided for modifying the fatty acid content of a plant, plant part or plant tissue, such as an oil-producing plant tissue. The method may comprise the steps of: introducing a heterologous DNA sequence encoding ADS1 or ADS2 into a plant cell, to produce a transformed cell; culturing the transformed cell or progeny of the transformed cell to generate a transgenic plant; and maintaining the transgenic plant under conditions so that the transgenic plant produces transgenic tissue wherein the DNA is expressed. The ratio of oleic acid to stearic acid in the transgenic tissue, or in the tissue of a progeny of the transgenic plant, may thereby be modified relative to the fatty acid content of a tissue from a control oil-producing plant, further modifications as characterized above may be made in alternative embodiments.

Another aspect of the invention provides transgenic plant cells, plant parts and plant tissues derived from such plant cells, and descendants thereof. Recombinant gene constructs comprising ADS1 or ADS2 may be introduced into the genome of the desired plant host by a variety of conventional techniques which include, without limitation, electroporation and microinjection of plant cell prototplasts and polyethylene glycol precipitation (such as are disclosed in Paszkowski et al., 1984, Embo J. 3: 2717–2722; Fromm et al., 1985, Proc. Natl. Acad. Sci. (USA) 82: 5824; and in U.S.

Pat. Nos. 4,684,611; 4,801,540; 4,743,548 and 5,231,019), ballistic methods such as DNA particle bombardment (for example as disclosed in Klein et al., 1987, Nature 327:70–73; Gordon-Kamm, et al. (1990); and in U.S. Pat. Nos. 4,945,050; 5,015,580; 5,149,655 and 5,466,587); Agrobacterium-mediated transformation methods (such as those disclosed Horsch et al., 1984, Science 233: 496–498; Fraley et al., 1983, Proc. Natl. Acad. Sci. (USA) 80:4803; and U.S. Pat. Nos. 4,940,838 and 5,464,763). Alternative transformation protocols are disclosed for example in U.S. Pat. No. 5,584,807; 5,501,967; Fraley et al., 1982, *Proc. Natl. Acad. Sci. USA* 79:1859–1863; Krens et al., 1982, *Nature* 296:72–74).

Transformed plant cells, which may be derived by any of the above transformation techniques, may be cultured to regenerate whole plants having the transformed genotype and displaying a desired phenotype, as for modified ratios of oleic acid to stearic acid. A variety of plant culture techniques may be used to regenerate whole plants, such as described in: Gamborg and Phillips (Eds), Plant Cell, Tissue and Organ Culture—Fundamental Methods (Springer Lab Manual), 1995; Evans et al., Protoplasts Isolation and Culture, Handbook of Plant Cell Culture, Macmillan Publishing Company, New York, pp. 124–176 (1983); Klee et al., Ann. Rev. of Plant Phys. 38: 467–486 (1987).

In some aspects of the invention, nucleic acids encoding ADS1 or ADS2 proteins may be introduced into plants by transformation, and expression of such nucleic acids may be mediated by promoters to which such coding sequences are operably linked. In the context of the present invention, "promoter" means a sequence sufficient to direct transcription of a gene when the promoter is operably linked to the gene. The promoter is accordingly the portion of a gene containing DNA sequences that provide for the binding of RNA polymerase and initiation of transcription. Promoter sequences are commonly, but not universally, located in the 5' non-coding regions of a gene. A promoter and a gene are "operably linked" when such sequences are functionally connected so as to permit gene expression mediated by the promoter. The term "operably linked" accordingly indicates that DNA segments are arranged so that they function in concert for their intended purposes, such as initiating transcription in the promoter to proceed through the coding segment of a gene to a terminator portion of the gene. Gene expression may occur in some instances when appropriate molecules (such as transcriptional activator proteins) are bound to the promoter. Expression is the process of conversion of the information of a coding sequence of a gene into mRNA by transcription and subsequently into polypeptide (protein) by translation, as a result of which the protein is said to be expressed. As the term is used herein, a gene or nucleic acid is "expressible" if it is capable of expression under appropriate conditions in a particular host cell.

For the present invention, promoters may be used that provide for preferential gene expression within a specific organ or tissue, or during a specific period of development. For example, promoters may be used that are specific for embryogenesis (U.S. Pat. No. 5,723,765 issued Mar. 3, 1998 to Oliver et al.). Such promoters may, in some instances, be obtained from genomic clones of cDNAs. Depending upon the application of the present invention, those skilled in this art may choose a promoter for use in the invention which provides a desired expression pattern. Promoters may be identified from genes which have a differential pattern of expression in a specific tissue by screening a tissue of interest, for example, using methods described in U.S. Pat. No. 4,943,674 and European Patent Application EP-A 0255378.

One of skill will recognize that after the nucleic acid is stably incorporated in transgenic plants, it may be introduced into other plants by sexual crossing. Any of a number of standard breeding techniques may be used for such crosses, depending upon the species to be crossed.

In various embodiments, the invention comprises genetically modified plants, which may express ADS1 or ADS2. In some embodiments, such plants will exhibit altered fatty acid content in one or more parts or tissues. These aspects of the invention relate to all higher plants, including monocots and dicots, such as species from the genera Fragaria. Lotus, Medicago, Onobrychis, Triforium, Trigonelia, Vigna, Citrus, Linum. Geranium, Manihot, Caucus, Arabidopsis, Brassica, Raphanus, Sinapis, Atropa, Capsicum, Hyoscyamus, Lycopersicon, Nicotiana, Solanum, Petunia, Digitalis, Majorana, Cichorium, Helianthus, Lactuca, Bromus, Asparagus, Antirrhinum, Heterocatlis, Nemesia, Pelargonium, Panicum, Penniserum, Ranunculus, Senecio, Salpiglossis, Cucarnis, Browallia, Glycine, Lolium, Zea, Triticum, Sorghum, and Datura. Such plants may include maize, wheat, rice, barley, soybean, beans, rapeseed, canola, alfalfa, flax, sunflower, cotton, clover, lettuce, tomato cucurbits, potato carrot, radish, pea lentils, cabbage, broccoli, brussel sprouts, peppers, apple, pear, peach, apricot, carnations and roses. More specifically, in alternative embodiments, plants for which the invention may be used in modifying fatty acid content include oil crops of the Cruciferae family: canola, rapeseed (Brassica spp.), crambe (Crambe spp.), honesty (Lunaria spp.) lesquerella (Lesquerela spp.), and others; the Composirae family: sunflower (Helianthus spp.), safflower (Carthamus spp.), niger (Guizotia spp.) and others; the Palmae family: palm (Elaeis spp.), coconut (Cocos spp.) and others; the Leguminosae family: peanut (Arachis spp.), soybean (Glycine spp.) and others; and plants of other families such as maize (Zea spp.), cotton (Gossypium sp.), jojoba (Simonasia sp.), flax (Linum sp.), sesame (Sesamum spp.), castor bean (Ricinus spp.), olive (Olea spp.), poppy (Papaver spp.), spurge (Euphorbia, spp.), meadowfoam (Limnanthes spp.), mustard (Sinapis spp.) and cuphea (Cuphea spp.).

Procedures for analysis of fatty acid composition are known in the art. These procedures can be used to identify individual transgenic or genetically modified plants to be retained in a breeding program of the invention as well as to determine the fatty acid composition of the plant part, such as oil, obtained from plants of the invention. For example, the fatty acid composition of control or transgenic plant seeds may be determined by extracting the oil, preparing fatty acid methyl esters, and then separating and quantitating the fatty acid methyl esters by conventional procedures, such as by gas-liquid chromatography.

In other embodiments of the invention, ADS1 or ADS2 may be used in conjunction with an additional lipid-modifying enzyme. For example, ADS1 or ADS2 may be used with a keto-acyl synthase. In such embodiments, the keto-acyl synthase may be used to shift lipid composition from palmitic acid to stearic acid (U.S. Pat. No. 5,510,255), so that a further shift from stearic to oleic acid may be mediated by ADS1 or ADS2 to provide a high oleic acid content, such as a high oleic acid oil.

The following examples are illustrative only of various embodiments of the invention, and are not exhaustive nor intended to limit the invention.

EXAMPLE 1
Cloning of the DNA Fragment of ORF Encoding the Arabidopsis ADS1 Gene The open reading frame of the ADS1 gene was cloned by PCR using Arabidopsis cDNA as a template. The total cDNA isolated from a cDNA library was a gift from Dr. Pat Covello (NRC, Plant Biotechnology Institute, Canada). The original Arabidopsis cDNA library was sent as a gift to Dr. Covello by Dr. Ronald Davis (Stanford University, Calif.). The construction of the Arabidopsis cDNA library and isolation of plasmids containing total cDNAs were done according to standard method (Elledge et al., 1991; Proc. Natl. Acad. Sci. USA 88: 1731–1735). PCR primers (ADS1up: 5'TCGGATCCCAAGATGTCATTGTCAGCCTC3', SEQ ID NO: 3; ADS1low: 5'AATGTCTAGACGTCGTTC CATATCTTCAA3', SEQ ID NO: 4) were designed according to the ADS1 sequence previously reported (Fukuchi-Mizutani et al., 1998), which were flanking the ORF and 3'-UTR of ADS1 with BamHI restriction site included in ADS1up and XbaI site included in ADS1low. The PCR reaction was performed in a total volume of 100 ul, which contained 20 ng cDNA, 1 mM dATP, 1 mM dCTP, 1 mM dGTP, 1 mM dTTP, 50 mM KCl, 10 mM Tris pH 8.3, 1.5 mM $MgCl_2$ and 1 unit of Taq DNA polymerase enzyme. The amplification was done with 30 cycles using the following cycling parameters: 30 s at 95° C., 30 s at 56° C., 1 min at 72° C. The PCR mixture was incubated at 72° C. for 10 min after cycling and the DNA was denatured for 5 min at 95° C. before amplification.

The PCR products were fractionated on a 1% agarose gel in TBE running buffer with the 1 kb DNA ladders (BRL) as DNA size marker. The amplified fragment (~940 bp) was extracted from the gel slice using the GlassMAX DNA Isolation Spin Cartridge System (BRL), which was then cloned into a TA cloning vector pCR2.1-TOPO according to the manufacture's instructions (Invitrogen). The resulting plasmid, pKNY100, was used to verify the ADS1 insert sequence. The ADS1 fragment was sequenced on both strands by a PRISM DyeDeoxy™ Teminator Cycle Sequencing Kit using a 377 DNA Sequencer. Sequence analysis was performed with the Lasergne DNA software kit (DNASTAR Inc.) The analysis confirmed that the ADS1 open reading frame cloned by PCR was identical to the sequence reported previously ((Fukuchi-Mizutani et al., 1998).

EXAMPLE 2
Plasmid Construction

In order to express the ADS1 gene in a seed specific manner, in this example the napin promoter was used as the regulatory sequence in the gene construct for plant transformation. For this purpose, the ADS1 gene was re-amplified using pKNY100 as template. The primer pairs were ADS1up-1: 5'TGTCTAGAGATGTCATTGTCAGC-CTCGGA3' (SEQ ID NO: 5) and ADS1low-1: 5'TCG-GATCCTCAACGAACCATTGCCATACG3' (SEQ ID NO: 6), which contained XbaI site and BamHI site, respectively. PCR reactions were the same as in example 1 except that Taq DNA polymerase (Phamacia) was replaced by Pfu DNA polymerase (BRL). This allows the re-amplification of ADS1 ORF.

A plant transformation vector pSE129A, where a squalene epoxidase gene in antisense orientation was placed under the transcriptional control of napin promoter (Covello et al., 1998, 13$^{th}$ International Symposium on Plant Lipids, Sevilla, Spain.), was used as donor binary vector to make the gene construct. The napin promoter sequence (1145 bp up from ATG start codon) used in pSE129A was amplified by PCR using primers prepared based on the published sequence. After extraction of the PCR fragment, the DNA was digested with restriction enzymes XbaI and BamHI. The vector pSE129A was also digested by XbaI and BamHI to remove the squalene epoxidase gene. The ADS1 fragment was then ligated to the digested pSE129A. The resulting plasmid was termed pRB01, in which the ADS1 gene was placed under the transcriptional control of napin promoter. After transformation of E. coli, strain DH5α, the plasmid was verified by sequencing the whole insert from napin promoter to NOS terminator. Finally, the Agrobacterium tumefaciens, strain GV3101, was transformed with pRB01 by electroporation using electroporator (BioRad) according to the manufacturer's instructions. Agrobacterium transformants were selected on 2YT plate containing 50 ug/ml of Kanamycin and 25 ug/ml Gentamycin.

EXAMPLE 3
Brassica juncea Transformation

Rapeseed is one of the most important crops worldwide. Although Brassica napus and Brassica rapa constitute the majority of rapeseed production in North America, Brassica juncea (Indian mustard) offers alternative species to the rapeseed/canola production because of its unique superior agronomic traits including heat and drought tolerances. Therefore, in this invention we chose Brassica juncea as a model plant system for transformation in order to evaluate the ADS1 gene function, its physiological role and potential application. Specifically, the breeding line J96D-4830, a germplasm proprietary to the Saskatchewan Wheat Pool, was used as donor plant for transformation. J96D-4830 was a homozygous line obtained through doubled haploid techniques.

Brassica juncea transformants were obtained by Agrobacteria mediated transformation according to protocols reported previously with modifications (Moloney et al., 1989; Plant Cell Reports 6: 321–325). Briefly, seeds of J96D-4830 were surface sterilized and grown in solid media containing 1/2×MS basal media (Sigma), pH 5.6, 1% sucrose and 0.7% phytagar (BRL) under sterile conditions for 10 days. On the 8$^{th}$ day, cultures of Agrobacteria harboring plasmid pRB 01 were grown overnight in LB media containing 50 ug/ml kanamycin and 25 ug/ml gentamycin at 28° C. Hypocotyls of the juncea J96D-4830 were cut into ~1 cm segments, exposed to the Agrobacteria culture that was diluted 100 times in filter sterilized 1×MS basal media containing 3% sucrose and 100 ug/ml acetosyringone, pH 8.0, for 10 min. Then the hypocotyls were plated out onto co-cultivation media (1×MS, 3% sucrose, 1.8% mannitol, 0.7% phytagar, 1 ug/ml 2,4-D, 3 mM MES, pH 5.6) for a 3 day period. The hypocotyls were transferred to fresh co-cultivation media containing 300 ug/ml Timentin for 7 days to clean up the residual Agrobacteria. Hypocotyls were then transferred to selection/regeneration media (1×MS, 3% sucrose, 300 ug/ml Timentin 0.7% phytagar, 15 ug/ml kanamycin3 ug/ml N$^6$-benzyladenine, pH 5.8). Hypocotyls were transferred to fresh selection/regeneration media every three weeks for a total of three transfers for shoot development. Regenerated shoots were transferred to elongation media (1×MS, 3% sucrose, 300 ug/ml Timentin 0.7% phytagar, 15 ug/ml kanamycin, 0.5 ug/ml N$^6$-benzyladenine, pH 5.8) for 2 weeks. Elongated shoots were transferred to rooting media (1×MS, 3% sucrose, 300 ug/ml Timentin 0.7% phytagar, 15 ug/ml kanamycin, 0.2 ug/ml indole-3-butyric acid, pH 5.8) for 3 weeks. Finally, all regenerated plants (T$_0$) which were resistant to kanamycin were transferred to soil and maintained under the following growth conditions in greenhouse until seeds ($T_1$) were harvested: 25° C. with light for 16 h and 20° C. without light for 8 h.

EXAMPLE 4

Screening of $T_0$ Transformants by PCR

All putative transgenic plants were screened by PCR to confirm the existence of transgene. Total genomic DNA was isolated from leaves following the protocols described previously (Dellaporta et al., 1983. Plant Molecular Biol. Reporter 1:19–21). The gene coding for neophosphotransferase II (NPTII) was used as the target for PCR amplification using primers NPT1 (5'-TTGAACAAGATGGATTGCACGCAGG-3', SEQ ID NO: 7) and NPT2 (5'-CGCCAAGCTCTTCAGCAATATCACG-3', SEQ ID NO: 8). The PCR were performed in a total volume of 20 ul which contained 50 ng of total leaf DNA, 8 ng of each primer, 0.2 mM dATP, 0.2 mM dTTP, 0.2 mM dCTP, 0.2 mM dGTP, 50 mM KCl, 10 mM Tris pH 8.3, 1.5 mM MgCl2 and 1 unit of Taq DNA polymerase (Pharmacia). Total DNA isolated from leaves of wild type J96D-4830 was used as negative control. The samples were pre-heated for 5 min at 95° C. to denature DNA followed by 30 cycles under the cycling conditions: 80" at 95° C., 2' at 55° C., 2' at 72° C. The PCR mixture was incubated at 72° C. for 10 min after cycling. PCR products were separated on a 0.8% agarose gel in TAE buffer using 1 kb DNA ladders as size markers (BRL).

PCR results indicated that out of 49 putative transgenic lines 33 lines were positive. Three randomly selected PCR negative lines were kept under growth conditions until seeds were harvested and these negative control seeds were analyzed as controls. The rest of the PCR negative lines were discarded.

EXAMPLE 5

Lipid Extraction and Fatty Acid Analysis

Seeds from transgenic plants were harvested at the maturity stage and analyzed for fatty acid composition. For each sample, 10 seeds were homogenized for oil extraction and triplicates of each transgenic line were analyzed. Specifically, 10 mature seeds were weighed out and placed into a plastic vial that contains a stainless metal rod (Profast'ners, Saskatoon, Saskatchewan). To each plastic vial, 2 ml of 0.5 N sodium methoxide in methanol (Fisher, Nepean, Ontario) and 1 ml of hexane that contained 500 ug tripentadecanoin (TAG, C-15:0; Sigma, St. Louis Mo.) as internal standard. The vial was capped well and shaken for 20 min at low speed using a Eberbach Shaker (Eberbach, Ann Arbour, Mich.). After homogenization of seeds the sample vials were kept on bench for another 30 min for oil extraction. Then 1 ml of distilled water was added to each vial. The sample vials were centrifuged for 5 min at 3,500 rpm using a bench top centrifuge, Baxter Canlab Megafuge 1.0 (Heraeus Instruments). 200 ul of the top layer was transferred into an auto-sampler vial and 0.9 ml of hexane added to each vial. The sample was then analyzed by the gas-liquid chromatography (GLC).

The GLC analysis was accomplished with a Hewlett Packard 5890 gas liquid chromatograph equipped with a DB-23 column (0.25 mm inner diameter×30 m long; company) and flame ionization detector. The parameters for the GLC operation include injector temperature of 250° C. and detector temperature of 300° C. Helium was used as a carrier gas whose flow rate was 1 ml/min. The eluted fatty acid methyl esters were integrated and identity of each peak was confirmed by comparison with authentic standards. Standard fatty acid methyl esters were all purchased from Sigma, which include palmitic acid (16:0), palmitoleic acid (16:1, Δ9) stearic acid (18:0), oleic acid (18:1, Δ9), vaccenic acid (18:1, Δ11), linoleic acid (18:2), linolenic acid (18:3), arachidic acid (20:0), eicosenoic acid (20:1), behenic acid (22:0) and erucic acid (22:1).

EXAMPLE 6

Fatty Acid Composition of Transgenic *Brassica juncea*

Figure 2:
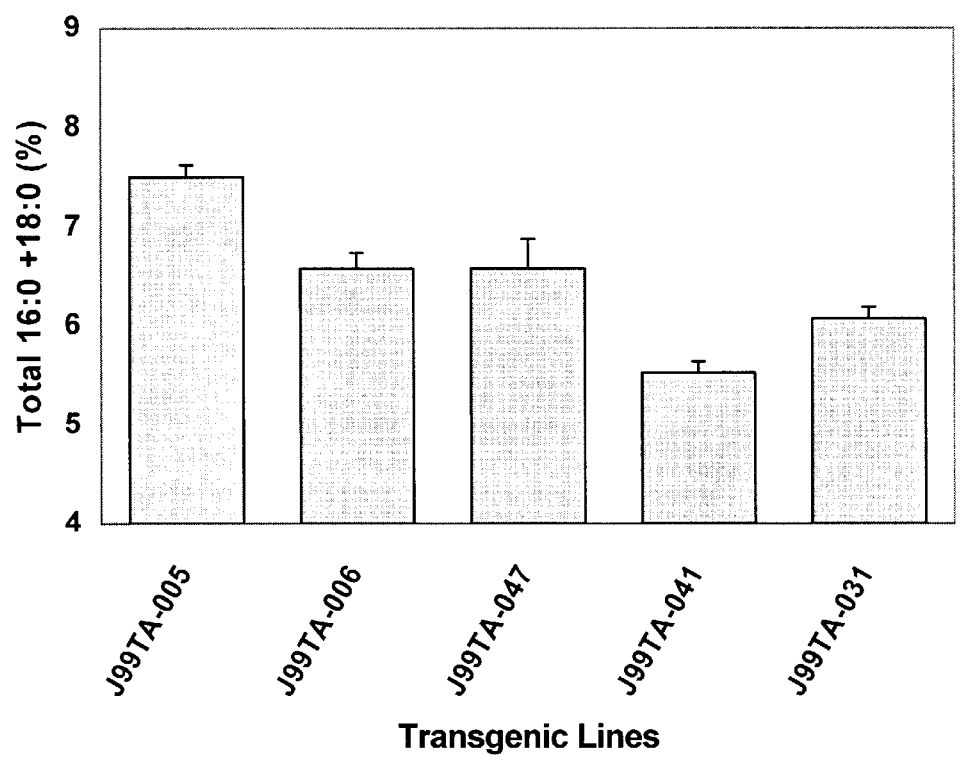
FIG. 2 is a bar graph showing the results of the experiments of Examples 5 and 6, showing changes of the percentage of the sum of palmitic acid (16:0) and stearic acid (18:0) in the representative T1 seeds of transgenic lines. ADS1 Positive lines are J99TA-31 and J99TA-41 (multiple copies ADS1). ADS1 Negative Lines are J99TA-05, J99TA-06 and J99TA-47.
Figure 3:
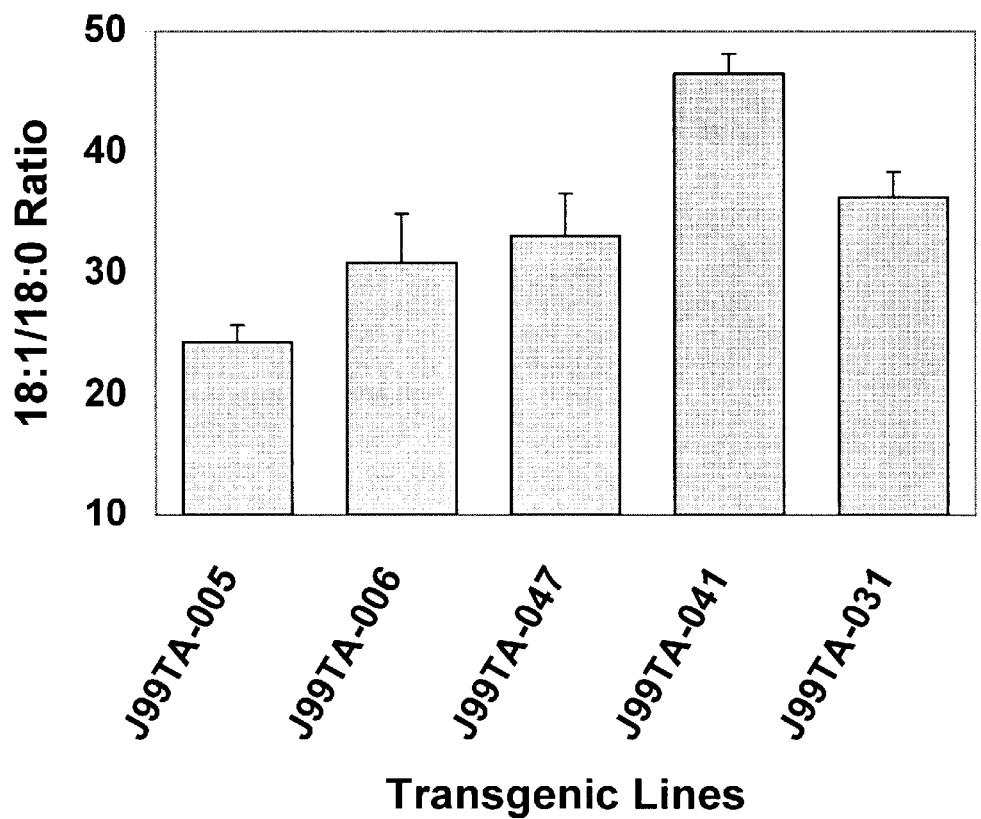
FIG. 3 is a bar graph showing the results of the experiments of Examples 5 and 6, showing changes of the ratio of oleic acid (18:1) to stearic acid (18:0) in the representative T1 seeds of transgenic lines. ADS1 Positive lines are J99TA-31 and J99TA-41 (multiple copies ADS1). ADS1 Negative Lines are J99TA-05, J99TA-06 and J99TA-47.
Figure 4:
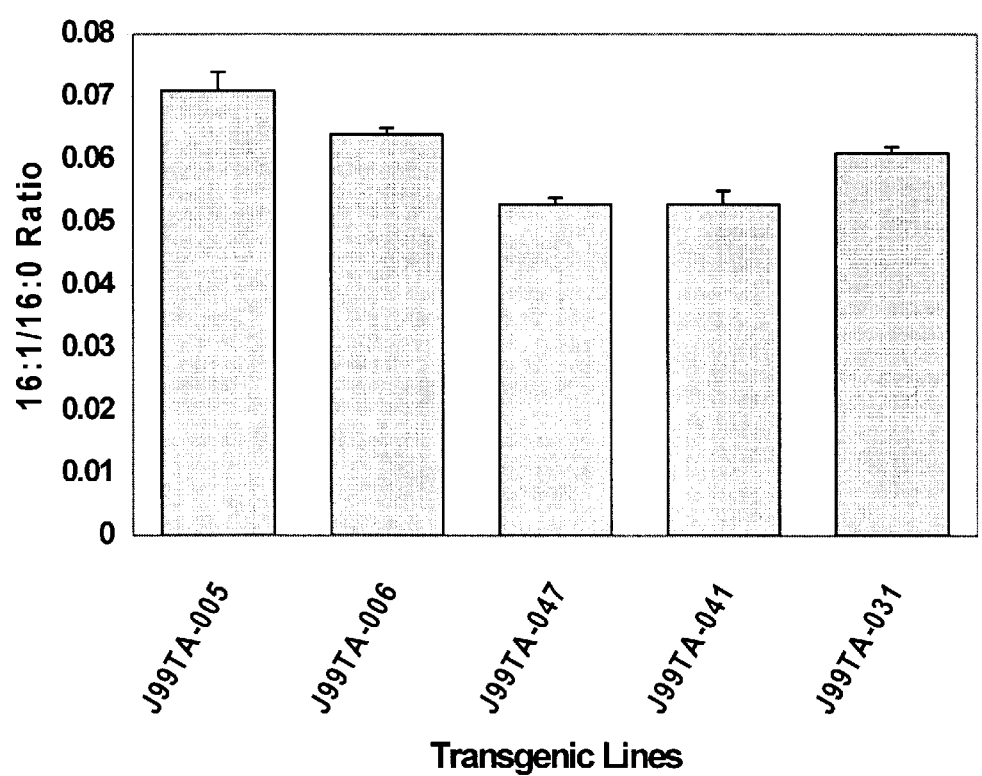
FIG. 4 is a bar graph showing the results of the experiments of Examples 5 and 6, showing changes of the ratio of palmitoleic acid (16:1) to palmitic acid (16:0) in the representative T1 seeds of transgenic lines. ADS1 Positive lines are J99TA-31 and J99TA-41 (multiple copies ADS1). ADS1 Negative Lines are J99TA-05, J99TA-06 and J99TA-47.
Figure 5:
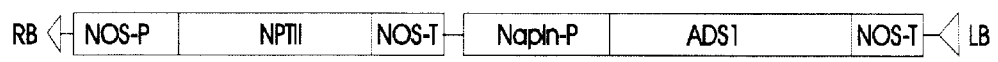
FIG. 5 is a functional map of the plasmid pRB01 used in the Brassica transformation experiments. NOS-P, nopaline synthase promoter; NPTII, gene encoding neomycin phosphotransferase II that confers resistance to kanamycin; NOS-T, nopaline synthase terminator; ADS1, the Arabidopsis gene encoding Δ9 acyl-CoA fatty acid desaturase; Napin-P, napin promoter; RB and LB, right and left border sequences, respectively, which serve as signals for T-DNA transfer.

Fatty acid composition of seed oils was calculated as percentage of total fatty acids (Table 1 and FIGS. 1 through 4). Transgenic lines J99TA-41 and J99TA-31 showed a significant reduction in the level of saturated fatty acids (sum of 16:0, 18:0, 20:0 and 22:0) in seed oil compared to control lines (J99TA-005, J99TA-006, and J99TA-047) (Table 1, FIG. 1). The reduction in the level of saturated fatty acids can be mainly attributed to the reduction of 16:0 and 18:0 (FIG. 2). When the ratios of products over substrates of the transgene ADS1 were compared, there was a significant increase in the 18:1/18:0 ratio but not in the 16:1/16:0 ratio (FIGS. 3 and 4). These results show that the ADS1 gene codes for an acyl-CoA desaturase, which prefers stearoyl-CoA to palmitoyl-CoA as substrate.

TABLE 1

Fatty Acid Composition of Transgenic *Brassica juncea* expressed as percentage of total fatty acids in mature seeds.

| Sample Name | 16:0 (%) | 16:1 (%) | 18:0 (%) | 18:1 (%) | 18:2 (%) | 18:3 (%) | 20:0 (%) | 20:1 (%) | 20:2 (%) | 22:0 (%) | 22:1 (%) |
|---|---|---|---|---|---|---|---|---|---|---|---|
| J99TA-031 | 4.56 | 0.28 | 1.62 | 54.77 | 21.12 | 14.71 | 0.51 | 1.17 | 0.10 | 0.28 | 0.00 |
| J99TA-031 | 4.62 | 0.28 | 1.48 | 56.04 | 20.36 | 14.40 | 0.47 | 1.19 | 0.09 | 0.26 | 0.00 |
| J99TA-031 | 4.44 | 0.27 | 1.50 | 55.83 | 20.27 | 14.85 | 0.47 | 1.21 | 0.09 | 0.25 | 0.00 |
| Average | 4.54 | 0.28 | 1.53 | 55.55 | 20.58 | 14.65 | 0.48 | 1.19 | 0.10 | 0.26 | 0.00 |
| J99TA-041 | 4.29 | 0.23 | 1.22 | 57.36 | 20.77 | 13.44 | 0.41 | 1.23 | 0.10 | 0.23 | 0.00 |
| J99TA-041 | 4.37 | 0.24 | 1.28 | 57.29 | 19.45 | 14.64 | 0.43 | 1.24 | 0.09 | 0.25 | 0.00 |
| J99TA-041 | 4.21 | 0.22 | 1.22 | 58.45 | 20.21 | 12.83 | 0.42 | 1.35 | 0.10 | 0.23 | 0.04 |
| Average | 4.29 | 0.23 | 1.24 | 57.70 | 20.14 | 13.64 | 0.42 | 1.27 | 0.10 | 0.24 | 0.01 |
| J99TA-005 | 5.26 | 0.36 | 2.16 | 50.74 | 23.90 | 14.48 | 0.62 | 1.06 | 0.10 | 0.35 | 0.00 |
| J99TA-005 | 5.80 | 0.42 | 1.79 | 45.20 | 28.60 | 14.98 | 0.59 | 1.07 | 0.12 | 0.38 | 0.00 |
| Average | 5.53 | 0.39 | 1.98 | 47.97 | 26.25 | 14.73 | 0.60 | 1.06 | 0.11 | 0.36 | 0.00 |
| Std. Dev. | 0.38 | 0.05 | 0.27 | 3.91 | 3.32 | 0.36 | 0.03 | 0.01 | 0.01 | 0.02 | 0.00 |
| J99TA-006 | 4.88 | 0.31 | 1.58 | 53.33 | 23.23 | 13.78 | 0.49 | 1.18 | 0.10 | 0.27 | 0.00 |
| J99TA-006 | 4.81 | 0.31 | 1.88 | 52.56 | 23.05 | 14.38 | 0.56 | 1.13 | 0.10 | 0.30 | 0.00 |
| Average | 4.85 | 0.31 | 1.73 | 52.95 | 23.14 | 14.08 | 0.53 | 1.16 | 0.10 | 0.28 | 0.00 |
| Std. Dev. | 0.05 | 0.00 | 0.21 | 0.54 | 0.13 | 0.43 | 0.05 | 0.03 | 0.01 | 0.02 | 0.00 |

TABLE 1-continued

Fatty Acid Composition of Transgenic *Brassica juncea* expressed as percentage of total fatty acids in mature seeds.

| | | | | | | | | | | | |
|---|---|---|---|---|---|---|---|---|---|---|---|
| J99TA-047 | 4.97 | 0.27 | 1.82 | 55.59 | 22.14 | 12.07 | 0.58 | 1.15 | 0.11 | 0.32 | 0.00 |
| J99TA-047 | 4.76 | 0.25 | 1.60 | 56.90 | 21.12 | 12.22 | 0.54 | 1.26 | 0.11 | 0.30 | 0.00 |
| Average | 4.87 | 0.26 | 1.71 | 56.24 | 21.63 | 12.15 | 0.56 | 1.20 | 0.11 | 0.31 | 0.00 |
| Std. Dev. | 0.15 | 0.01 | 0.15 | 0.92 | 0.72 | 0.10 | 0.03 | 0.08 | 0.00 | 0.01 | 0.00 |
| Average of Controls | 5.08 | 0.32 | 1.80 | 52.39 | 23.67 | 13.65 | 0.57 | 1.14 | 0.11 | 0.32 | 0.00 |

| Sample Name | 16:0 + 18:0 (%) | Sat (%) | 18:1/18:0 | 16:1/16:0 | 16:0/18:0 | 18:1/16:1 | (18:1/18:0)(16:1/16:0) |
|---|---|---|---|---|---|---|---|
| J99TA-031 | 6.18 | 6.96 | 33.9 | 0.0620 | 2.82 | 193.82 | 546 |
| J99TA-031 | 6.10 | 6.83 | 37.8 | 0.0605 | 3.11 | 200.52 | 625 |
| J99TA-031 | 5.94 | 6.66 | 37.2 | 0.0608 | 2.96 | 206.78 | 612 |
| Average | 6.07 | 6.82 | 36.29 | 0.0611 | 2.96 | 200.27 | 594 |
| J99TA-041 | 5.51 | 6.15 | 47.0 | 0.0528 | 3.52 | 253.12 | 891 |
| J99TA-041 | 5.65 | 6.33 | 44.7 | 0.0553 | 3.41 | 237.06 | 809 |
| J99TA-041 | 5.43 | 6.08 | 47.9 | 0.0523 | 3.45 | 265.68 | 917 |
| Average | 5.53 | 6.19 | 46.56 | 0.0535 | 3.46 | 251.50 | 871 |
| J99TA-005 | 7.42 | 8.39 | 23.4 | 0.0682 | 2.43 | 141.47 | 344 |
| J99TA-005 | 7.59 | 8.55 | 25.3 | 0.0728 | 3.25 | 107.04 | 347 |
| Average | 7.50 | 8.47 | 24.37 | 0.0705 | 2.84 | 122.85 | 346 |
| Std. Dev. | 0.12 | 0.11 | 1.31 | 0.00 | 0.58 | 24.35 | 3 |
| J99TA-006 | 6.46 | 7.22 | 33.7 | 0.0627 | 3.09 | 174.28 | 538 |
| J99TA-006 | 6.69 | 7.55 | 28.0 | 0.0645 | 2.57 | 169.36 | 435 |
| Average | 6.58 | 7.39 | 30.88 | 0.0636 | 2.83 | 171.80 | 486 |
| Std. Dev. | 0.16 | 0.23 | 4.03 | 0.00 | 0.37 | 3.48 | 73 |
| J99TA-047 | 6.79 | 7.69 | 30.6 | 0.0537 | 2.74 | 208.14 | 570 |
| J99TA-047 | 6.36 | 7.21 | 35.5 | 0.0524 | 2.97 | 228.00 | 678 |
| Average | 6.58 | 7.45 | 33.07 | 0.0531 | 2.85 | 217.73 | 623 |
| Std. Dev. | 0.30 | 0.34 | 3.46 | 0.0009 | 0.16 | 14.04 | 76.22 |
| Average of Controls | 6.89 | 7.77 | 29.44 | 0.062 | 2.84 | 171.19 | 485 |

ADS1 Positive lines: J99TA-31 and J99TA-41 (multiple copies). ADS1 Negative Lines: J99TA-05, J99TA-06, J99TA-47.

EXAMPLE 7
Southern Blot Analysis of Transgene in Plant Transformants

All PCR positive lines and negative lines were further analyzed by Southern blot hybridization using ADS1 as probe. For this purpose, total genomic DNA was isolated from leaves of each line according to the protocol described in Example 3. For Southern blot analysis, 20 ug of total genomic DNA was digested with HindIII followed by separation on a 0.8% agarose gel. The transfer of separated DNA to nylon membrane, probe preparation and hybridization were performed according to standard protocols (Ausubel et al., 1999, Short Protocols in Molecular Biology, 4$^{th}$ edition). Hybridization and washes were performed under high stringent conditions to eliminate non-specific hybridization. The Southern blot analysis results were consistent with the PCR results, confirming that no hybridization was detected in the PCR negative lines and that hybridization was detected in every positive line. The number of transgene insertions ranged from a single copy to 5 copies. The ADS1 gene was present in lines J99TA-41 and J99TA-31 and not present in lines J99TA-05, J99TA-06 and J99TA-47. The J99TA-41 line contained multiple copies of ADS1 and the J99TA-31 line contained a single copy of ADS1.

EXAMPLE 8
Expression of ADS1 in Transgenic Lines

Expression of ADS1 gene in transgenic lines was measured by reverse transcriptase-polymerase chain reaction (RT-PCR). Total RNA was isolated from developing siliques of transgenic lines, wild type and negative control lines using TRIzol reagent (BRL) according to the manufacture's protocols. 1 ug of total RNA was used in the RT reaction using SuperScript™ II reverse transcriptase (BRL). The RT reactions were primed with primer ADS1low (SEQ ID NO: 4) and incubated at 42° C. for 50 min followed by heat inactivation at 70° C. for 15 min. 2 ul from each 20 ul RT reaction was used in a 50 ul total volume PCR reaction using Taq DNA polymerase (BRL).

In the presence of reverse transcriptase in an RT reaction, a 940 bp fragment was amplified from all the transgenic lines. Without reverse transcriptase in the RT reaction, no amplification was detected from any of the transgenic lines, indicating that the PCR amplification results from RNA and is reverse transcriptase-dependent. No amplification was detected from negative lines. The results confirm that ADS1 gene is indeed expressed in *B. juncea* transformed using the gene construct pRB01 and that the altered fatty acid profile in these transgenic lines is due to the expression of the ADS1 gene.

Conclusion

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A method for modifying a dicot plant, comprising the steps of:

a) introducing a DNA sequence encoding an ADS1 Δ9 fatty acid desaturase into a plant cell of the dicot plant, or an ancestor of the dicot plant, to produce a genetically modified dicot plant comprising the DNA sequences, i) wherein the DNA sequence encodes an ADS1 Δ9 fatty acid desaturase having at least 95% sequence identity to an Arabidopsis ADS1 Δ9 fatty acid desaturase, or ii) wherein the DNA sequence has at least 95% sequence identity to the sequence of SEQ ID NO: 1;

b) maintaining the genetically modified dicot plant under conditions so that the DNA sequence encoding the ADS1 Δ9 fatty acid desaturase is expressed; and so that the ratio of oleic acid (18:1) to stearic acid (18:0) is increased by at least 20% in a part of the genetically modified dicot plant, compared to a corresponding part of a non-modified dicot plant, and so that the ratio of palmitoleic acid (16:1) to palmitic acid (16:0) is decreased or remains unchanged or is increased by no more than 20% in the part of the genetically modified dicot plant, compared to the corresponding part of the non-modified dicot plant.

2. The method as claimed in claim 1, wherein the genetically modified dicot plant is a Brassica species and wherein the ratio of oleic acid to stearic acid in the part of the genetically modified dicot plant is about 35 or greater and the ratio of palmitoleic acid to palmitic acid is about 0.1 or less in the part of the genetically modified dicot plant.

3. The method of claim 2, wherein the part of the genetically modified dicot plant is a seed.

4. The method of claim 3, wherein the DNA sequence is introduced into the dicot plant cell by electroporation, microparticle bombardment, microinjection, or Agrobacterium-mediated transformation.

5. The method of claim 1, wherein the DNA sequence encodes Arabidopsis ADS1.

6. The method of claim 1, wherein the dicot plant is a Brassica species.

7. The method of claim 6, wherein the plant part is an oil extracted from a mature seed of the genetically modified dicot plant.

8. A genetically modified dicot plant comprising a heterologous DNA sequence encoding an ADS1 Δ9 fatty acid desaturase, wherein the DNA sequence encodes an ADS1 Δ9 fatty acid desaturase having at least 95% sequence identity to an Arabidopsis ADS1 Δ9 fatty acid desaturase, or wherein the DNA sequence has at least 95% sequence identity to the sequence of SEQ ID NO: 1; and wherein the DNA sequence encoding the ADS1 Δ9 fatty acid desaturase is expressed so that the ratio of oleic acid (18:1) to stearic acid (18:0) is increased by at least 20% in a part of the genetically modified dicot plant, compared to a corresponding part of a non-modified dicot plant, and so that the ratio of palmitoleic acid (16:1) to palmitic acid (16:0) is decreased or remains unchanged or is increased by no more than 20% in the part of the genetically modified dicot plant, compared to the corresponding part of the non-modified dicot plant.

9. The genetically modified dicot plant as claimed in claim 8, wherein the dicot plant is a Brassica species and the ratio of oleic acid to stearic acid in the part of the genetically modified plant is about 35 or greater and the ratio of palmitoleic acid to palmitic acid is about 0.1 or less in the part of the genetically modified dicot plant.

10. The genetically modified dicot plant as claimed in claim 9, wherein the part of the genetically modified dicot plant is a seed.

11. The genetically modified dicot plant as claimed in claim 8, wherein the DNA sequence encodes Arabidopsis ADS1.

12. The genetically modified dicot plant as claimed in claim 8, wherein the dicot plant is a Brassica species.

13. The genetically modified dicot plant of claim 12, wherein the plant part is an oil extracted from a mature seed of the genetically modified dicot plant.

14. The method of claim 1, wherein the DNA sequence has the sequence of SEQ ID NO: 1.

15. The genetically modified dicot plant of claim 8, wherein the DNA sequence has the sequence of SEQ ID NO: 1.

16. The method of claim 6, wherein the Brassica species is *Brassica napus*.

17. The method of claim 6, wherein the Brassica species is *Brassica rapa*.

18. The method of claim 6, wherein the Brassica species is *Brassica juncea*.

19. The genetically modified dicot plant of claim 12, wherein the Brassica species is *Brassica napus*.

20. The genetically modified dicot plant of claim 12, wherein the Brassica species is *Brassica rapa*.

21. The genetically modified dicot plant of claim 12, wherein the Brassica species is *Brassica juncea*.

22. A method for modifying a *Brassica juncea* plant, comprising the steps of:

a) introducing a DNA sequence encoding an Arabidopsis ADS1 Δ9 fatty acid desaturase, or having the sequence of SEQ ID NO: 1, into a plant cell of the *Brassica juncea* plant, or an ancestor of the *Brassica juncea* plant, to produce a genetically modified *Brassica juncea* plant comprising the DNA sequence;

b) maintaining the genetically modified *Brassica juncea* plant under conditions so that the DNA sequence encoding the Arabidopsis ADS1 Δ9 fatty acid desaturase, or having the sequence of SEQ ID NO: 1, is expressed; and so that the ratio of oleic acid (18:1) to stearic acid (18:0) is increased by at least 20% in a part of the genetically modified *Brassica juncea* plant, compared to a corresponding part of a non-modified *Brassica juncea* plant, and so that the ratio of palmitoleic acid (16:1) to palmitic acid (16:0) is decreased or remains unchanged or is increased by no more than 20% in the part of the genetically modified *Brassica juncea* plant, compared to the corresponding part of the non-modified *Brassica juncea* plant.

23. The method as claimed in claim 22, wherein the ratio of oleic acid to stearic acid in the part of the genetically modified *Brassica juncea* plant is about 35 or greater and the ratio of palmitoleic acid to palmitic acid is about 0.1 or less in the part of the genetically modified *Brassica juncea* plant.

24. The method of claim 23, wherein the part of the genetically modified plant is a seed.

25. The method of claim 24, wherein the DNA sequence is introduced into the plant cell by electroporation, microparticle bombardment, microinjection, or Agrobacterium-mediated transformation.

26. The method of claim 22, wherein the plant part is an oil extracted from a mature seed of the genetically modified plant.

27. A genetically modified *Brassica juncea* plant comprising a heterologous DNA sequence encoding an Arabidopsis ADS1 Δ9 fatty acid desaturase or having the sequence of SEQ ID NO: 1; wherein the DNA sequence is expressed so that the ratio of oleic acid (18:1) to stearic acid (18:0) is increased by at least 20% in a part of the genetically modified *Brassica juncea* plant, compared to a corresponding part of a non-modified *Brassica juncea* plant, and so that the ratio of palmitoleic acid (16:1) to palmitic acid (16:0) is decreased or remains unchanged or is increased by no more than 20% in the part of the genetically modified *Brassica*

*juncea* plant, compared to the corresponding part of the non-modified *Brassica juncea* plant.

28. The genetically modified *Brassica juncea* plant as claimed in claim 27, wherein the ratio of oleic acid to stearic acid in the part of the genetically modified *Brassica juncea* plant is about 35 or greater and the ratio of palmitoleic acid to palmitic acid is about 0.1 or less in the part of the genetically modified *Brassica juncea* plant.

29. The genetically modified plant as claimed in claim 28, wherein the part of the genetically modified plant is a seed.

30. The genetically modified plant of claim 27, wherein the plant part is an oil extracted from a mature seed of the genetically modified plant.

* * * * *

UNITED STATES PATENT AND TRADEMARK OFFICE
CERTIFICATE OF CORRECTION

PATENT NO. : 6,737,564 B2
DATED : May 18, 2004
INVENTOR(S) : Yao et al.

It is certified that error appears in the above-identified patent and that said Letters Patent is hereby corrected as shown below:

<u>Title page,</u>
Insert Item:

-- [30]  Foreign Application Priority Data

Mar. 21, 2001  (CA)............................ 2,340,998 --

Signed and Sealed this

Twenty-first Day of September, 2004

JON W. DUDAS
*Director of the United States Patent and Trademark Office*

SEQUENCE LISTING

<160> NUMBER OF SEQ ID NOS: 10

<210> SEQ ID NO 1
<211> LENGTH: 1178
<212> TYPE: DNA
<213> ORGANISM: Arabidopsis thaliana

<400> SEQUENCE: 1

```
ccacaaagag tcttttttt ttttctcttc gacttagctt atacatagtt ttattacaag      60
atgtcattgt cagcctcgga gaaggaggag aataacaaga aaatggcagc ggacaaggct     120
gagatgggga ggaagaagag ggcaatgtgg gaaagaaagt ggaagagatt ggacattgtg     180
aaagcttttg catctctctt tgtccatttc ctctgtctct tggcgccttt caatttcact     240
tggccggctt taagagtcgc cctcattgtc tatacggtgg gtgggctcgg tatcaccgtc     300
tcttaccacc gaaatttggc tcaccggagc ttcaaagtcc ctaaatggct cgagtatttc     360
ttcgcttatt gcggccttct tgccattcag ggagatccga ttgattgggt gagcacacat     420
cgataccatc accagtttac agattcggat agggaccccac atagtcctaa cgaaggattt    480
tggttcagtc acctcctatg gctatttgat accggttatc ttgtagaaaa gtgtggaaga    540
aggacaaatg tggaggactt aaagaggcag tggtactata aattcctcca agaacagtc     600
ctttaccaca ttctaacatt tggtttcctc ctctattact ttggtggttt gtcttttctt    660
acttggggaa tgggtattgg ggtagcaatg gagcatcatg tgacttgcct cataaactct    720
ctttgccatg tttggggaag ccgaacttgg aagactaatg acacttcccg taacgtttgg    780
tggctatcag tattctcgtt tggagagagc tggcacaaca atcaccacgc cttcgaatcc    840
tcggcgagac aaggcttaga atggtggcaa atcgacattt cttggtatat tgtccgcttt    900
ctcgagatta tcggtttggc tactgatgtt aagttgcctt ccgagagtca acgtcgtcgt    960
atggcaatgg ttcgttgaag atatggaacg acgtctcgtc tcatttaagc attagttaat   1020
taatgtctac gtacgttta agttttttggt aaacgtaaca cttgtaatat tgtgcgatgc   1080
ggtgttgttt tgtgacttgt ggtgtgtgtt tgaaccaact tgcttaatta agataacgtt   1140
cgttttgata tgagcgaaaa aaaaaaaaaa aaaaaaaa                            1178
```

<210> SEQ ID NO 2
<211> LENGTH: 1156
<212> TYPE: DNA
<213> ORGANISM: Arabidopsis thaliana

<400> SEQUENCE: 2

```
gagaagagaa agagagatcc gaaatgtcgg tgacatcaac ggtggaggag aaccaccaga     60
aaaatccatc aacgccggcg gcggtggagg agaagaagaa gaggagatgg gtgttttggg    120
atagaaggtg gaggagatta gattatgtga aattctcagc ttctttcact gttcattctc    180
ttgctctctt ggctccgttt tatttcactt ggtcggctct tgggttacg ttttttgtttt    240
acaccatcgg tggtcttggt atcaccgtct cttatcatcg caacttggct caccggagtt    300
tcaaagtccc taaatggctt gagtatctct tagcctattg tgcccttctc gctattcagg    360
gagatccgat tgattgggtg agtacacatc gttaccatca ccagttcacg gattcagaac    420
```

```
gtgatccaca tagtcctaag gaaggttttt ggtttagtca tcttctttgg atctatgact      480
ctgcctatct tgtttcaaag tgtggaagaa gagcaaacgt ggaggatttg aagaggcaat      540
ggttttatag gtttcttcag aaaacagtgc tatttcacat tttaggattg ggtttctttc      600
tcttctacct tggtggcatg tccttcgtta cttggggaat gggggtagga gcagcattgg      660
aagtgcacgt gacttgcctc ataaattcac tctgccatat ttggggcact cgaacttgga      720
agaccaatga cacttctcgt aatgtttggt ggttatcggt attttcattt ggagagagtt      780
ggcacaacaa tcatcatgcg ttcgagtcat cggctagaca aggacttgaa tggtggcaaa      840
tagacatttc gtggtacatt gttcggtttt tcgaaattat cggtttagcg accgatgtga      900
aagtgccaac ggaggctcaa cgacgtcgta tggctatagt tcgttgatgg aaattgcggg      960
aagagcatag aaaaagggat ctattctatg taattagaat aatttctaat cctaaaagag     1020
agttattgtt ttattttctt tattactact tttgaagttt tgggttaacg caaaggacgt     1080
ttccgatgtg ttttggtgtt ggaccaagtt gattaagata tttgtcgtaa aaaaaaaaa     1140 aaaaaaaaaa ctcgag                                                     1156

<210> SEQ ID NO 3
<211> LENGTH: 29
<212> TYPE: DNA
<213> ORGANISM: Arabidopsis thaliana

<400> SEQUENCE: 3
tcggatccca agatgtcatt gtcagcctc                                         29

<210> SEQ ID NO 4
<211> LENGTH: 29
<212> TYPE: DNA
<213> ORGANISM: Arabidopsis thaliana

<400> SEQUENCE: 4
aatgtctaga cgtcgttcca tatcttcaa                                         29

<210> SEQ ID NO 5
<211> LENGTH: 29
<212> TYPE: DNA
<213> ORGANISM: Arabidopsis thaliana

<400> SEQUENCE: 5
tgtctagaga tgtcattgtc agcctcgga                                         29

<210> SEQ ID NO 6
<211> LENGTH: 29
<212> TYPE: DNA
<213> ORGANISM: Arabidopsis thaliana

<400> SEQUENCE: 6
tcggatcctc aacgaaccat tgccatacg                                         29

<210> SEQ ID NO 7
<211> LENGTH: 25
<212> TYPE: DNA
<213> ORGANISM: Unknown
<220> FEATURE:
<223> OTHER INFORMATION: Description of Unknown Organism: NPT1 primer
      for NPTII

<400> SEQUENCE: 7
ttgaacaaga tggattgcac gcagg                                             25
```

<210> SEQ ID NO 8
<211> LENGTH: 25
<212> TYPE: DNA
<213> ORGANISM: Unknown
<220> FEATURE:
<223> OTHER INFORMATION: Description of Unknown Organism:NPT2 primer for NPTII

<400> SEQUENCE: 8
cgccaagctc ttcagcaata tcacg         25

<210> SEQ ID NO 9
<211> LENGTH: 305
<212> TYPE: PRT
<213> ORGANISM: Arabidopsis thaliana

<400> SEQUENCE: 9

```
Met Ser Leu Ser Ala Ser Glu Lys Glu Asn Asn Lys Lys Met Ala
 1               5                  10                  15

Ala Asp Lys Ala Glu Met Gly Arg Lys Lys Arg Ala Met Trp Glu Arg
             20                  25                  30

Lys Trp Lys Arg Leu Asp Ile Val Lys Ala Phe Ala Ser Leu Phe Val
             35                  40                  45

His Phe Leu Cys Leu Leu Ala Pro Phe Asn Phe Thr Trp Pro Ala Leu
         50                  55                  60

Arg Val Ala Leu Ile Val Tyr Thr Val Gly Gly Leu Gly Ile Thr Val
 65                  70                  75                  80

Ser Tyr His Arg Asn Leu Ala His Arg Ser Phe Lys Val Pro Lys Trp
                 85                  90                  95

Leu Glu Tyr Phe Phe Ala Tyr Cys Gly Leu Leu Ala Ile Gln Gly Asp
             100                 105                 110

Pro Ile Asp Trp Val Ser Thr His Arg Tyr His His Gln Phe Thr Asp
         115                 120                 125

Ser Asp Arg Asp Pro His Ser Pro Asn Glu Gly Phe Trp Phe Ser His
     130                 135                 140

Leu Leu Trp Leu Phe Asp Thr Gly Tyr Leu Val Glu Lys Cys Gly Arg
145                 150                 155                 160

Arg Thr Asn Val Glu Asp Leu Lys Arg Gln Trp Tyr Tyr Lys Phe Leu
                 165                 170                 175

Gln Arg Thr Val Leu Tyr His Ile Leu Thr Phe Gly Phe Leu Leu Tyr
             180                 185                 190

Tyr Phe Gly Gly Leu Ser Phe Leu Thr Trp Gly Met Gly Ile Gly Val
         195                 200                 205

Ala Met Glu His His Val Thr Cys Leu Ile Asn Ser Leu Cys His Val
     210                 215                 220

Trp Gly Ser Arg Thr Trp Lys Thr Asn Asp Thr Ser Arg Asn Val Trp
225                 230                 235                 240

Trp Leu Ser Val Phe Ser Phe Gly Glu Ser Trp His Asn Asn His His
                 245                 250                 255

Ala Phe Glu Ser Ser Ala Arg Gln Gly Leu Glu Trp Trp Gln Ile Asp
             260                 265                 270

Ile Ser Trp Tyr Ile Val Arg Phe Leu Glu Ile Ile Gly Leu Ala Thr
         275                 280                 285

Asp Val Lys Leu Pro Ser Glu Ser Gln Arg Arg Met Ala Met Val
     290                 295                 300
```

-continued

```
Arg
305

<210> SEQ ID NO 10
<211> LENGTH: 306
<212> TYPE: PRT
<213> ORGANISM: Arabidopsis thaliana

<400> SEQUENCE: 10

Met Ser Val Thr Ser Thr Val Glu Glu Asn His Gln Lys Asn Pro Ser
  1               5                  10                  15

Thr Pro Ala Ala Val Glu Glu Lys Lys Lys Arg Arg Trp Val Phe Trp
             20                  25                  30

Asp Arg Arg Trp Arg Arg Leu Asp Tyr Val Lys Phe Ala Ser Phe Thr
         35                  40                  45

Val His Ser Leu Ala Leu Leu Ala Pro Phe Tyr Phe Thr Trp Ser Ala
     50                  55                  60

Leu Trp Val Thr Phe Leu Phe Tyr Thr Ile Gly Gly Leu Gly Ile Thr
 65                  70                  75                  80

Val Ser Tyr His Arg Asn Leu Ala His Arg Ser Phe Lys Val Pro Lys
                 85                  90                  95

Trp Leu Glu Tyr Leu Leu Ala Tyr Cys Ala Leu Leu Ala Ile Gln Gly
            100                 105                 110

Asp Pro Ile Asp Trp Val Ser Thr His Arg Tyr His His Gln Phe Thr
        115                 120                 125

Asp Ser Glu Arg Asp Pro His Ser Pro Lys Glu Gly Phe Trp Phe Ser
    130                 135                 140

His Leu Leu Trp Ile Tyr Asp Ser Ala Tyr Leu Val Ser Lys Cys Gly
145                 150                 155                 160

Arg Arg Ala Asn Val Glu Asp Leu Lys Arg Gln Trp Phe Tyr Arg Phe
                165                 170                 175

Leu Gln Lys Thr Val Leu Phe His Ile Leu Gly Leu Gly Phe Phe Leu
            180                 185                 190

Phe Tyr Leu Gly Gly Met Ser Phe Val Thr Trp Gly Met Gly Val Gly
        195                 200                 205

Ala Ala Leu Glu Val His Val Thr Cys Leu Ile Asn Ser Leu Cys His
    210                 215                 220

Ile Trp Gly Thr Arg Thr Trp Lys Thr Asn Asp Thr Ser Arg Asn Val
225                 230                 235                 240

Trp Trp Leu Ser Val Phe Ser Phe Gly Glu Ser Trp His Asn Asn His
                245                 250                 255

His Ala Phe Glu Ser Ser Ala Arg Gln Gly Leu Glu Trp Trp Gln Ile
            260                 265                 270

Asp Ile Ser Trp Tyr Ile Val Arg Phe Phe Glu Ile Ile Gly Leu Ala
        275                 280                 285

Thr Asp Val Lys Val Pro Thr Glu Ala Gln Arg Arg Arg Met Ala Ile
    290                 295                 300

Val Arg
305
```